United States Patent [19]

Knudsen

[11] Patent Number: 4,528,415
[45] Date of Patent: Jul. 9, 1985

[54] ETHYLENE DIMERIZATION

[75] Inventor: Ronald D. Knudsen, Bartlesville, Okla.

[73] Assignee: Phillips Petroleum Company, Bartlesville, Okla.

[21] Appl. No.: 642,007

[22] Filed: Aug. 20, 1981

Related U.S. Application Data

[62] Division of Ser. No. 517,108, Jul. 25, 1983, Pat. No. 4,487,847.

[51] Int. Cl.$^3$ .............................................. C07C 2/02
[52] U.S. Cl. .................................. 585/527; 585/511; 585/514
[58] Field of Search ....................... 585/511, 514, 527

[56] References Cited

U.S. PATENT DOCUMENTS

| | | | |
|---|---|---|---|
| 3,424,816 | 1/1969 | McClure et al. | 585/511 |
| 3,497,488 | 2/1970 | Dawans et al. | 502/155 |
| 3,535,397 | 10/1970 | Schott | 585/370 |
| 3,564,072 | 2/1971 | Butte | 585/513 |
| 3,644,564 | 2/1972 | Zwet et al. | 585/520 |
| 3,808,246 | 4/1974 | Fahey | 585/259 |
| 4,118,408 | 10/1978 | Fahey et al. | 585/514 |

OTHER PUBLICATIONS

Fellmann et al., *JACS*, vol. 101, No. 14, Jul. 4, 1979, pp. 5099–5101; vol. 103, 1981, pp. 5752–5758.
McClure et al., *Journal of Organometallic Chemistry*, 80, (1974), pp. 385–393.

*Primary Examiner*—Curtis R. Davis

[57] ABSTRACT

A novel ethylene dimerization catalyst is provided consisting essentially of a nickel compound, a phosphine compound, and an acidic compound. In addition, an improved ethylene dimerization process is provided which comprises contacting ethylene with the novel catalyst composition present, in an effective solvent, at a temperature from about 0° C. to about 200° C. As a result of the inventive precess, high catalyst productivity and good selectivity to the desired dimerized product, 1-butene, is obtained.

12 Claims, No Drawings

ETHYLENE DIMERIZATION

This application is a divisional of U.S. Ser. No. 517,108 filed July 25, 1983, now U.S. Pat. No. 4,487,847.

This invention relates to a novel catalyst for the dimerization of ethylene. This invention also relates to a novel process for the dimerization of ethylene to give 1-butene in high selectivity.

A variety of catalysts, both homogeneous and heterogeneous, have been utilized to dimerize ethylene to butene. For example U.S. Pat. No. 3,564,072 discloses a process for the dimerization of ethylene employing a catalyst formed by combining a nickel (II) phosphine coordination complex, an inorganic Lewis acid, and an excess of phosphine ligand.

U.S. Pat. No. 3,644,564 discloses the dimerization of ethylene in the presence of a catalyst comprising a nickel(0) compound complexed with fluorine containing ligands.

While the catalyst systems disclosed by the above references are operable for the dimerization of ethylene, they are merely typical of other dimerization catalysts known in the art. By using these and other known catalyst systems for the dimerization of ethylene, one has not always achieved high catalyst productivity, good selectivity to desired 1-butene product or a combination of both.

Because of the increasing importance that 1-butene is playing in the chemical industry, as exemplified by the importance of α-olefins, processes which make even slight improvements in the availability of 1-butenes over existing processes are highly desirable.

Therefore, it is an object of this invention to provide an improved catalyst for the dimerization of ethylene. A further object of this invention is to provide an improved process for the dimerization of ethylene. Yet another object of this invention is to provide a highly selective process for the dimerization of ethylene to give 1-butene.

Other aspects, objects and advantages of the present invention will become apparent from a study of this specification and the claims.

In accordance with one embodiment of the present invention, I have discovered a novel catalyst composition for the dimerization of ethylene which is highly productive and affords good selectivity to the desired 1-butene. This improved catalyst composition consists essentially of:

(a) at least one nickel compound selected from the group consisting of: bis(1,5-cyclooctadiene)nickel(0), bis(tricyclohexylphosphine)nickel(0), (cyclododecatriene)nickel, and bis(ethylene)(dicyclohexylphosphine)nickel;

(b) a phosphine compound of the formula $PR_3$ wherein each R independently represents H or a $C_1$ to $C_{20}$ hydrocarbyl radical with the proviso that any alkenyl substitution be at least 3 carbon atoms removed from the phosphorus atom and at least one R is not H; and (c) at least one acidic compound selected from the groups consisting of:
(i) a sulfonic acid of the formula $R'SO_3H$ wherein R' is H, or a fluorinated or nonfluorinated alkyl, aryl, alkaryl, or aralkyl radical with 1-10 carbon atoms; and
(ii) a carboxylic acid of the formula $R''COOH$ wherein R'' is at least a partially fluorinated alkyl, aryl, alkaryl, or aralkyl radical with 1-9 carbon atoms.

Exemplary of the phosphine compounds of the formula $PR_3$ are dicyclohexylphosphine, triphenylphosphine, and tris(4-fluorophenyl)phosphine. Preferred is dicyclohexylphosphine.

Examples of non-fluorinated sulfonic acids of the formula $R'SO_3H$ for use in the present invention are para-toluenesulfonic acid, benzenesulfonic acid, naphthalenesulfonic acid, methanesulfonic acid, and mixtures thereof.

Exemplary fluorinated sulfonic acids are trifluoromethanesulfonic acid, 4-fluorobenzenesulfonic acid, pentafluorobenzenesulfonic acid, 4-trifluoromethylbenzenesulfonic acid, and mixtures thereof.

Exemplary carboxylic acids are trifluoroacetic acid, heptafluorobutyric acid, pentafluorobenzoic acid, perfluoropropionic acid, and mixtures thereof.

While the order of addition of catalyst precursors is not thought to be critical in the present invention, preferably the inventive composition is made by contacting the catalyst precursors, i.e., a suitable nickel compound, and phosphine compound, each present in a suitable solvent as described in this specification, at room temperature for about 15 minutes. Subsequently the acidic compound, present in a suitable solvent, is added.

In the catalyst composition, the molar ratio of the phosphine ligand to the nickel compound can be broadly about 0.01–4.0 to 1, preferably about 0.5–2.5 to 1. The molar ratio of the particular acid compound used to the nickel compound should generally be about 0.01–10.0 to 1, preferably 0.05–2.0 to 1.

In accordance with another embodiment of the present invention I have discovered that ethylene is efficiently dimerized by contacting ethylene at a temperature from about 0° C. to about 200° C. with the catalyst composition described in an earlier embodiment of the present invention, said catalyst composition being present in at least one solvent selected from the group consisting of:

(i) an aromatic hydrocarbon of the formula

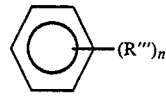

wherein R''' represents a $C_1$ to $C_6$ alkyl radical and n is 0, 1, 2, 3, or 4; and (ii) an alcohol of the formula $(R^{iv})_3COH$ wherein each $R^{iv}$ independently represents H or a $C_1$ to $C_{12}$ alkyl, cycloalkyl, aryl, alkaryl, or aralkyl radical.

After the inventive catalyst, present in at least one solvent, is prepared as described above, it is contacted with ethylene. The precise method of establishing ethylene/catalyst contact during the reaction is not critical. In one modification, the catalyst system is charged to an autoclave or other similar pressure (vessel) reactor, the ethylene is introduced, and the reaction mixture is maintained with agitation at reaction temperature and pressure for the desired reaction period.

Aromatic hydrocarbon solvents of the formula

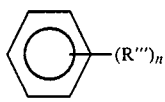

contemplated for use in the present invention include benzene, toluene, xylenes, trimethylbenzenes, ethylbenzenes, cumene and mixtures thereof. Toluene is presently preferred.

Exemplary alcohols of the formula $(R^{iv})_3COH$ include ethanol, 2-butanol, isobutanol, tertiary butanol, 2-pentanol, 1-hexanol and mixtures thereof. Presently preferred is 2-pentanol.

Whatever solvent is used, of course, must exist as a liquid at dimerization reaction conditions.

The weight ratio of the solvent employed to the combination of the nickel compound, phosphine compound and acid components can be broadly $1-10^6$ to 1 with the amount of the solvent used limited only by its cost, the ease of product recovery therefrom, the required reaction vessel size, and other practical considerations. The preferred weight ratio is about 5-10,000 to 1.

Broadly, reaction temperatures vary from about 0° C. to 200° C, Preferably from about 20° C. to 125° C.

The reaction pressure is not thought to be critical but typically varies from about 5-5000 psig, preferably from about 200-2000 psig.

The reaction time is broadly from about 1 minute to 18 hours, preferably from about 5 minutes to 5 hours.

The dimerization products are separated and recovered from the reaction mixture by conventional methods such as fractional distillation, selective extraction, and adsorption.

It is within the scope of this invention to employ a batchwise or continuous reaction system wherein ethylene is passed in a continuous manner into a reaction zone containing the inventive catalyst system while ethylene dimerization product mixture is concomitantly withdrawn from the reaction mixture.

The following examples further illustrate the present invention.

EXAMPLE I

All reactions described were carried out in a 300 mL stainless steel (316SS) Autoclave Engineers stirred tank reactor. The reactor was first charged with about 50 mL of solvent, sealed under nitrogen, then pressured with ethylene and vented to aid oxygen removal. Under a sweep of ethylene, bis(1,5-cyclooctadiene)nickel(0) [Ni(COD)] was added, typically 0.5 g dissolved in a minimum volume of solvent (typically toluene) was employed. Then, the desired amount of a phosphine compound was added, dissolved in a minimum volume of solvent. This mixture was stirred for about 15 minutes, internal standards (pentane and heptane, about 3 g each) added and finally the acid component to be employed was added, dissolved in a minimum volume of solvent. The reactor was then charged with ethylene to a predetermined pressure, and reaction allowed to proceed in the range of room temperature to about 80° C, heating or cooling provided as necessary. The reaction pressure employed was typically about 700 psig. The desired pressure was maintained by periodic incremental additions of ethylene with up to about 15 additions per run. When the reaction was complete, about 10 mL of 2,4-pentanedione was added to the reactor to quench the catalyst, then a liquid sample (about 5-10 mL) was collected in a 75 mL stainless steel pressure bomb and set aside for gas liquid chromatographic (GLC) analysis.

Then the reactor was cooled to below room temperature, the ethylene pressure vented, and the reactor contents purged with nitrogen before opening the vessel. The product mixture was weighed to determine weight gain and then filtered prior to GLC analysis. A 150'×0.01" glass or stainless steel capillary column coated with OV-101 was employed for sample analysis. Analysis conditions were 100° C. for two minutes after injection, followed by 32°/min temperature program up to 200° C. final column temperature.

The bomb sample was analyzed in two portions. A first sample was injected under pressure onto a 20'×¼' stainless steel column packed with 19% bis-2-methoxyethoxyethylene on 60/80 mesh chromosorb P. Isothermal analysis conditions at 40° C. with helium carrier gas gave the amount of light ($C_2-C_5$) hydrocarbons in the reactor mixture. Another aliquot of the first sample was injected under pressure onto a 12'×⅛" stainless steel column packed with 0.19% picric acid on 80/100 mesh Carbopak C maintained at 50° C. isothermal to determine the amount of isobutylene present in the $C_4$ fraction. Bomb contents were then cooled, vented and poured into an open vessel, then analyzed on a 150'×0.02 od (0.01 id) capillary column coated with OV-101 with helium carrier gas and temperature programming at 5° C./min starting at 20° C. up to a final temperature of 90° C. for heavy ($C_6$ and greater) hydrocarbons.

Reaction results are reported in terms of catalyst productivity, wt % $C_4$, and the % 1-butene in the $C_4$ fraction. Catalyst productivity is defined as the grams of oligomerized (i.e. $C_4$ and greater) product produced per gram of Ni per hour. The wt % $C_4$ is the wt % of $C_4$ of the total oligomerization product. Percent 1-butene in the $C_4$ fraction is measured by analyzing the $C_4$ fraction of the oligomerization product for 1-butene, 2-butenes and branched $C_4$ olefin.

EXAMPLE II

Effect of Acid

A series of reactions were carried out in 2-pentanol as solvent, with bis(1,5-cyclooctadiene)nickel(0) [Ni(COD)], dicyclohexylphosphine [DCH] or tris(4-fluorophenyl) phosphine [TFP] and a variety of acids, following the general procedure described above in Example I. Thus, 50 mL of 2-pentanol and reagents as listed in Table I were charged to the reactor. Reaction parameters and results are summarized in Table I.

TABLE I

| | | | | Reaction Parameters | | | | | |
|---|---|---|---|---|---|---|---|---|---|
| | Reagents, mmol | | | Time, | Temp., | Press., | Product- | Wt % | % 1-Butene in |
| Run | Acid | Phosphine* | Ni(COD) | min. | °C. | psig | ivity | $C_4$ | $C_4$ fraction |
| 1 | 4-Me($C_6H_4$)$SO_3$H,1.6 | DCH,1.5 | 1.5 | 55 | 55 | 700 | 1109 | 97.7 | 98.7 |
| 2 | 4-Me($C_6H_4$)$SO_3$H,2.2 | DCH,2.0 | 2.0 | 70 | 55 | 700 | 617 | 97.3 | 98.7 |
| 3 | 4-Me($C_6H_4$)$SO_3$H,1.9 | DCH,1.7 | 1.7 | 60 | 57 | 700 | 800 | 97.7 | 98.3 |

TABLE I-continued

| Run | Reagents, mmol Acid | Phosphine* | Ni(COD) | Reaction Parameters Time, min. | Temp., °C. | Press., psig | Productivity | Wt % C₄ | % 1-Butene in C₄ fraction |
|---|---|---|---|---|---|---|---|---|---|
| 4 | F₃CSO₃H,0.9 | DCH,0.9 | 0.8 | 50 | 55 | 700 | 3994 | NA** | 81.7 |
| 5 | F₃CCO₂H,1.9 | DCH,1.8 | 1.9 | 40 | 55 | 700 | 1243 | 40.4 | NA** |
| 6 | F₃CCO₂H,1.8 | DCH,1.8 | 1.8 | 90 | 56 | 700 | 1139 | 43.7 | NA** |
| 7 | F₃CCO₂H,1.8 | DCH,1.9 | 1.9 | 50 | 57 | 700 | 890 | 43.5 | 97.6 |
| 8 | 4-Me(C₆H₄)SO₃H,1.9 | TFP,1.7 | 2.0 | 120 | 54 | 700 | 185 | 98.4 | 83.7 |
| 9 | F₃CCO₂H,1.7 | TFP,1.7 | 1.7 | 90 | 55 | 700 | 85 | 94.6 | 88.4 |

*DCH = dicyclohexylphosphine
TFP = tris(4-fluorophenyl)phosphine
**Not analyzed

The results of these experiments demonstrate that 1-butene can be prepared in high yield and selectivity employing the catalysts of this invention. Note especially the outstanding results obtained with a sulfonic acid such as toluene sulfonic acid and a simple phosphine such as dicyclohexylphosphine.

EXAMPLE III

Effect of phosphine

A series of reactions were carried out in 2-pentanol as solvent with bis(1,5-cyclooctadiene)nickel(0) [Ni(COD)], an acid component, and a variety of phosphine components, following the general procedure set forth above in Example I. Thus, 50 mL of 2-pentanol and reagents as listed in Table II were charged to the reactor. Reaction parameters and results are summarized in Table II.

EXAMPLE IV

Effect of Solvent

A series of reactions were carried out with bis(1,5-cyclooctadine)nickel(0) [Ni(COD)], an acid component, a phosphine component and toluene or 2-pentanol solvent, following the general procedure set forth above. In all cases, 50 mL of solvent were employed, plus quantities of reagents as listed in Table III. Reaction parameters and results are summarized in Table III.

TABLE III

| Run | Solvent | Reagents, mmol Acid* | Phosphine** | Ni(COD) | Reaction Parameters Time, min. | Temp., °C. | Press., psig | Productivity | Wt % | % 1-Butene in C₄-Fraction |
|---|---|---|---|---|---|---|---|---|---|---|
| 1 | 2-pentanol | TMS,0.9 | DCH,0.9 | 0.8 | 50 | 55 | 700 | 3994 | NA*** | 81.7 |
| 2 | toluene | TMS,0.7 | DCH,0.7 | 0.7 | 20 | 55 | 700 | 11810 | NA*** | 88.9 |
| 3 | 2-pentanol | TSA,1.6 | DCH,1.5 | 1.5 | 55 | 55 | 700 | 1109 | 97.7 | 98.7 |
| 4 | 2-pentanol | TSA,2.2 | DCH,2.0 | 2.0 | 70 | 55 | 700 | 617 | 97.3 | 98.7 |
| 5 | 2-pentanol | TSA,1.9 | DCH,1.7 | 1.7 | 60 | 57 | 700 | 800 | 97.7 | 98.3 |
| 6 | toluene | TSA,2.2 | DCH,2.0 | 2.0 | 75 | 56 | 700 | 475 | 90.5 | 99.0 |
| 7 | 2-pentanol | TSA,1.9 | TFP,1.7 | 2.0 | 120 | 54 | 700 | 185 | 98.4 | 83.7 |
| 8 | toluene | TSA,1.9 | TFP,1.7 | 1.7 | 110 | 56 | 700 | 144 | 98.8 | 91.1 |

*TMS = trifluoromethanesulfonic acid
TSA = 4-toluenesulfonic acid
**DCH = dicyclohexylphosphine
TFP = tris(4-fluorophenyl)phosphine
***Not analyzed The results of these experiments demonstrate that both aromatic hydrocarbon solvents such as toluene and alcohol solvents such as 2-pentanol are effective for carrying out the inventive dimerization reaction.

TABLE II

| Run | Reagents, mmol Phosphine | Acid* | Ni(COD) | Reaction Parameters Time, min. | Temp., °C. | Press., psig | Productivity | Wt % C₄ | % 1-Butene in C₄-Fraction |
|---|---|---|---|---|---|---|---|---|---|
| 1 | (cy-C₆H₁₁)₂PH,1.5 | TSA,1.6 | 1.5 | 55 | 55 | 700 | 1109 | 97.7 | 98.7 |
| 2 | (cy-C6H₁₁)₂PH,2.0 | TSA,2.2 | 2.0 | 70 | 55 | 700 | 617 | 97.3 | 98.7 |
| 3 | (cy-C₆H₁₁)₂PH,1.7 | TSA,1.9 | 1.7 | 60 | 57 | 700 | 800 | 97.7 | 98.3 |
| 4 | PPh₃,1.9 | TSA,2.2 | 2.0 | 90 | 55 | 700 | 281 | 98.5 | 81.6 |
| 5 | [4-F(C₆H₄)]₃P,1.7 | TSA,1.9 | 2.0 | 120 | 54 | 700 | 185 | 98.4 | 83.7 |
| 6 | (cy-C₆H₁₁)₂PH,1.8 | TFA,1.9 | 1.9 | 40 | 55 | 700 | 1243 | 40.4 | NA** |
| 7 | (cy-C₆H₁₁)₂PH,1.8 | TFA,1.8 | 1.8 | 90 | 56 | 700 | 1139 | 43.7 | NA** |
| 8 | (cy-C₆H₁₁)₂PH,1.9 | TFA,1.8 | 1.9 | 50 | 57 | 700 | 890 | 43.5 | 97.6 |
| 9 | PPh₃,1.6 | TFA,1.7 | 1.6 | 65 | 55 | 700 | 99 | 91.8 | 91.3 |
| 10 | [4-F(C₆H₄)]₃P,1.7 | TFA,1.7 | 1.7 | 90 | 55 | 700 | 85 | 94.6 | 88.4 |

*TSA = 4-toluenesulfonic acid
TFA = trifluoroacetic acid
**Not analyzed

The results of these experiments demonstrate that several phosphines, including dicyclohexylphosphine, triphenylphosphine and tris(4-fluorophenyl)phosphine give excellent ethylene conversion with high selectivity to the desired α-olefin, 1-butene.

Reasonable variations and modifications are possible within the scope of the foregoing.

I claim:

1. A process for the oligomerization of ethylene which comprises contacting said ethylene with a catalyst composition in the liquid phase present in at least one solvent selected from the group consisting of:
(i) an aromatic hydrocarbon of the formula

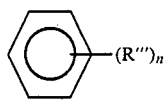

wherein each $R'''$ independently represents a $C_1$ to $C_6$ alkyl radical and n is 0, 1, 2, 3, or 4; and
(ii) an alcohol of the formula $(R^{iv})_3COH$ wherein each $R^{iv}$ independently represents H or a $C_1$ to $C_{12}$ alkyl, cycloalkyl, aryl, alkaryl, or aralkyl radical; the catalyst consisting essentially of:
(a) at least one nickel compound selected from the group consisting of:
bis(1,5-cyclooctadiene)nickel(0);
bis(tricyclohexylphosphine)nickel(0);
(cyclododecatriene)nickel; and
bis(ethylene)(dicyclohexylphosphine)nickel;
(b) a phosphine compound of the formula $PR_3$ wherein each R independently represents H or a $C_l$ to $C_{20}$ hydrocarbyl radical with the proviso that any alkenyl substitution be at least 3 carbon atoms removed from the phosphorus atom and at least one R is not H; and
(c) an acidic compound selected from the groups consisting of
(i) a sulfonic acid of the formula $R'SO_3H$ wherein $R'$ is H, or a fluorinated or non-fluorinated alkyl, aryl, alkaryl, or aralkyl radical with 1–10 carbon atoms.

2. A process according to claim 1 carried out at a temperature of from about 0° C. to about 200° C.

3. A process according to claim 1 wherein said solvent is one selected from the group consisting of benzene, toluene, xylenes, trimethylbenzenes, ethylbenzenes, and cumene.

4. A process according to claim 1 wherein said solvent is toluene.

5. A process according to claim 1 wherein said solvent is one selected from the group consisting of ethanol, 2-pentanol, t-butanol, iso-butanol, 2-butanol, and 2-hexanol.

6. A process according to claim 1 wherein said solvent is 2-pentanol.

7. A process according to claim 1 wherein said nickel compound is bis(1,5-cyclooctadiene)nickel(O).

8. A process according to claim 1 wherein said phosphine compound is one selected from the group consisting of triphenylphosphine, tris(4-fluorophenyl)phosphine, and dicyclohexylphosphine.

9. A process according to claim 1 wherein said phosphine compound is dicyclohexylphosphine.

10. A process according to claim 1 wherein said acid is p-toluenesulfonic acid.

11. A process according to claim 1 wherein said acid is trifluoromethanesulfonic acid.

12. A process according to claim 1 wherein the molar ratio of (b) to (a) of said composition is about 0.5–2.5 to 1 and the molar ratio of (c) to (a) of said composition is about 0.01–10.0 to 1.

* * * * *